United States Patent [19]

Taenzer

[11] 4,237,901
[45] Dec. 9, 1980

[54] LOW AND CONSTANT PRESSURE TRANSDUCER PROBE FOR ULTRASONIC DIAGNOSTIC SYSTEM

[75] Inventor: Jon C. Taenzer, Palo Alto, Calif.

[73] Assignee: Picker Corporation, Northford, Conn.

[21] Appl. No.: 938,072

[22] Filed: Aug. 30, 1978

[51] Int. Cl.³ .............................................. A61B 10/00
[52] U.S. Cl. ......................................... 128/660; 73/644
[58] Field of Search .................................. 128/660–663, 128/24 A; 73/644

[56] References Cited

U.S. PATENT DOCUMENTS

| 3,640,271 | 2/1972 | Horton | 128/662 |
| 4,033,178 | 7/1977 | Holt et al. | 73/644 |
| 4,059,098 | 11/1977 | Murdock | 73/644 X |

FOREIGN PATENT DOCUMENTS

| 760897 | 7/1953 | Fed. Rep. of Germany | 73/644 |
| 2418631 | 10/1975 | Fed. Rep. of Germany | 128/24 A |

Primary Examiner—Lee S. Cohen
Attorney, Agent, or Firm—Watts, Hoffmann, Fisher & Heinke Co.

[57] ABSTRACT

A diagnostic ultrasound real time B-scanner system has an improved probe assembly for fluid coupling a movable axis transducer to a patient's body. Pressure is maintained both low and constant by means of a passive pressure compensation apparatus. The probe includes apparatus containing the transducer and a fluid medium and including a compliant subject contacting bag. Pressure exerted by the bag on a subject is a function of (1) the pressure exerted on the fluid medium and (2) the orientation of the probe, due to the shifting weight of the fluid. The passive pressure compensator apparatus includes a gravity actuated apparatus for varying the pressure on the fluid medium as a function of the spatial orientation of the probe. This pressure variation compensates for the weight of the fluid medium and stabilizes the coupling pressure on the surface of the patient's body.

19 Claims, 5 Drawing Figures

LOW AND CONSTANT PRESSURE TRANSDUCER PROBE FOR ULTRASONIC DIAGNOSTIC SYSTEM

BACKGROUND OF THE INVENTION

1. Field of the Invention

This invention relates to the field of diagnostic ultrasonic systems and techniques. In such systems, an ultrasonic transducer is mounted in a probe assembly which supports the transducer, and which contains a fluid medium for establishing fluid coupling between the transducer and the patient. The transducer is movable by either an electrical or mechanical scanning means. The actual subject contacting element is a highly compliant bag which communicates with the fluid medium, and which is pressed against the patient's body during an ultrasonic study.

Imaging electronics coupled to the transducer processes electrical signals which the transducer generates in response to ultrasonic echoes. These echoes return to the transducer in response to transducer emitted ultrasonic energy reflecting from interfaces within the patient between tissue masses having differing acoustical impedance characteristics.

Position indicating circuitry produces electrical signals indicating the position and orientation of the transducer. Display apparatus is provided which responds to the transducer location indications and to the processed electrical signals from the transducer, to produce a real time image of a portion of the patient.

Such a system is suitable for use in examining a patient in what is known as a "B-scanning" technique. By way of example, a known type of ultrasound real time B-scannng system is described in U.S. patent application Ser. No. 725,178 by Green, et al, now U.S. Pat. No. 4,141,347, which is herein expressly incorporated by reference. B-scan systems are also described in an article by Green, P. S., "Methods of Acoustic Visualization", *International Journal of Non-destructive Testing,* Vol I (1969), pp, 1–27.

2. Description of the Prior Art

Scanning systems such as described above are used in examination of the carotid arteries of patients, to assess the patient's vascular condition and detect the presence and severity of arteriosclerosis. In addition to these scanning capabilities, such systems often also incorporate known apparatus and circuitry for implementing so called "Doppler" studies, to indicate blood volume and velocity within studied vessels.

The transducer is held in an ultrasonic probe assembly, which effects a fluid coupling between the transducer and the patient's skin, to maximize the efficiency of ultrasonic energy transfer from the transducer into the patient's body. A known type of transducer probe assembly is illustrated in FIG. 1 of the accompanying drawings.

In FIG. 1 an ultrasonic scanning transducer T is shown mounted within a rigid generally cylindrical, water filled structure S. The probe assembly also includes, at the lower end of the cylinder S, a highly compliant subject contact element known as a "coupling bag" B. The coupling bag communicates with the water within the cylindrical structure S. An additional compliant reservoir R is attached to the upper end of the cylindrical structure S. The reservoir R also communicates with the water in the structure S. The compliant bag B and reservoir R cooperate to afford a measure of resiliency in the fluid contact effected between the patient and bag.

The probe assembly illustrated in FIG. 1 suffers from at least two significant disadvantages. First, the pressure exerted on the patient's skin is a function of the spatial orientation of the probe. Secondly, and partially because of this undesirable position-related pressure variance, the coupling pressures used on patients must be high enough to effect an efficient coupling pressure for a variety of transducer probe orientations. A consequence of this is that, in certain transducer orientations, the coupling pressure is greater than that needed for efficient coupling.

In carotid artery studies, the patients often suffer from cardiovascular disease, including such things as prior heart attacks and strokes. Often, such patients have undesirable accumulations of fatty material in their arteries, as well as possible blood clots.

It is desirable to minimize and stabilize the coupling contact effected when a patient's arteries are examined, since this minimization also minimizes the likelihood that a blood clot or other piece of material may be dislodged because of mechanical pressure on the arteries.

Often, patients suffering from cardiovascular disease may be in a weakened condition, and, in such cases, it is frequently undesirable to require the patient to move or be moved about to different positions or attitude during the course of a study.

The prior art ultrasonic probe assembly, with its position-related coupling pressure variations, fails to maintain a coupling pressure which is suitably near the minimum desirable pressure for efficient coupling throughout a study. The fact that the patient often cannot or should not be moved about aggravates this problem, since, to follow an immobile patient's artery, the transducer probe must slide along a patient's skin and assume many widely differing attitudes.

The position-related coupling pressure variations come about as a result of the changing magnitude of the "head" of water exerting force on the coupling bag B. For example, when the probe is in a substantially vertical position, with the bag B facing downwardly, the pressure on the bag B is the entire weight of the vertical head of water represented by the arrows indicated as F1 in FIG. 1. If the probe assembly were to be turned horizontally, the shorter, or transverse, head of fluid would be applied, indicated as F2 in FIG. 1. Where the transducer probe assembly is inverted (which it sometimes must be to follow a patient's artery up under his chin) the pressure on the coupling bag B actually becomes negative, pulling the bag away from the skin and interfering with good ultrasonic coupling.

In order to maintain proper coupling over a variety of expected transducer probe orientations with the prior art probe, coupling pressures in the neighborhood of 0.5 pounds per square inch gauge must be employed. For reasons explained above, it would be an advantage to lower this pressure.

SUMMARY OF THE INVENTION

The present invention provides an improved design for a fluid coupled ultrasonic diagnostic system which solves the two problems of high pressure coupling and variation of coupling pressure by using a passive pressure balance technique and apparatus for the transducer probe assembly.

The invented system includes a mobile fluid coupled ultrasonic probe assembly having an ultrasonic transducer, an apparatus containing a fluid coupling medium and including a subject contact element for fluid coupling the transducer to a patient. The contact element exerts a force on the patient which is a function of the pressure on the fluid medium and the orientation of the probe assembly. The probe assembly further includes passive pressure compensating apparatus for varying the pressure on the fluid medium as a function of orientation of the assembly. The system further includes position and imaging elecronics and structure for processing electrical signals produced by the transducer in response to ultrasonic echoes, and transducer position representations, and display apparatus for utilizing the processed electrical signals and representations to generate an image of internal body structure of the patient.

According to a more specific aspect of the invention, the passive pressure compensating apparatus provides for the maintenance of a stable contact pressure on the patient's skin of substantially less than 0.5 PSIG, i.e., approximately 0.07 PSIG.

This invention thus enables an effective fluid coupling to be established between the patient's skin and the ultrasonic transducer for efficient system operation, while maintaining the contact pressure at a very low value, and holding the contact pressure substantially constant irrespective of the spatial orientation of the probe assembly.

In accordance with another specific aspect, the passive pressure compensation apparatus comprises a cylinder, a weighted piston slidably disposed in the cylinder and fluidicably coupled to the fluid medium, and resilient means for biasing the piston toward compression of the fluid medium in a predetermined magnitude.

Thus, the system contemplated in this invention has a gravity responsive, self-contained means for automatically varying the pressure applied to the fluid medium in response to changes in the orientation of the probe assembly. This system requires no external pressure maintenance apparatus, with attendant cumbersome and expensive components.

In accordance with another specific aspect, the resilient biasing means includes apparatus for adjusting its resiliency. This feature enables a user to regulate the level of the constant pressure maintained by the probe assembly in the transducer-patient fluid coupling.

In accordance with another specific feature, the subject contacting element comprises a highly compliant membrane forming a bag and communicating with the fluid coupling medium.

In accordance with another specific aspect, the passive pressure compensator apparatus is coupled fluidically to a liquid medium adjacent the contact element by way of a gaseous coupling medium. This feature reduces probe weight relative to such weight where all fluid media used are liquid.

The present invention, and its advantages, will be understood in more detail by reference to the following detailed description and the drawings, in which:

DESCRIPTION OF THE PREFERRED EMBODIMENT

Figure 1:
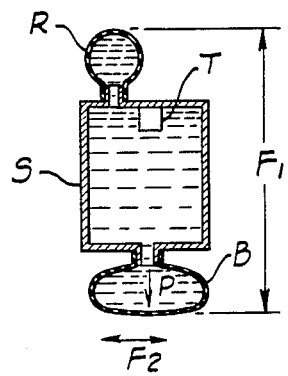
FIG. 1 is an elevational cross-sectional view of prior art apparatus.
Figure 2:
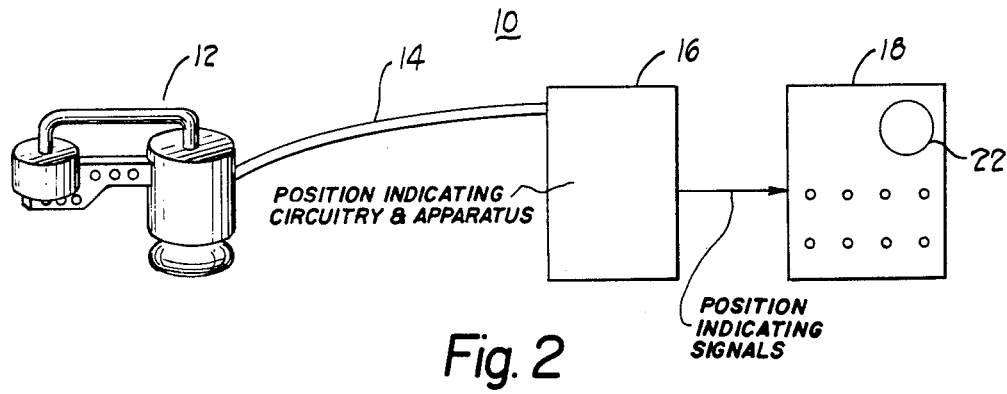
FIG. 2 is a graphical illustration of an ultrasonic system incorporating the present invention.

FIG. 2 shows a diagnostic ultrasonic system 10 incorporating the present invention. The diagnostic system 10 directs ultrasonic energy into a subject, such as a human patient, and detects ultrasonic echoes produced in response thereto. The system 10 utilizes the ultrasonic echoes to produce a visual image describing internal structure of the patient's body.

The system of FIG. 2 includes an ultrasonic probe assembly 12, imaging electronics 16 and a display apparatus 18.

The ultrasonic probe assembly 12 includes a known piezoelectric ultrasonic transducer with electronic or mechanical scanning means for reciprocally moving the transducer's propagation axis (not shown), and mounting structure for supporting the transducer, and a quantity of fluid medium for coupling it to the patient's skin surface. Power circuitry within the imaging electronics 16 actuates the transducer to propagate ultrasonic energy into the patient. The transducer senses ultrasonic echoes caused by the incident energy, and produces electrical signals representing those echoes.

Electrical signals from the power circuitry for actuating the transducer, and electrical signals produced by the transducer in response to ultrasonic echoes, travel between the transducer probe assembly 12 and the imaging electronics 16 by way of a multi-lead cable 14. The scanning means and associated circuitry produce position indicating electrical signals which represent the location and attitude of the transducer axis.

The imaging electronics 16 includes circuitry for processing electrical signals delivered to the imaging electronics from the transducer probe assembly 12. The processed electrical signals, and position indicating signals, are directed to a display apparatus 18, which suitably comprises a cathode ray oscilloscope. The cathode ray oscilloscope utilizes the processed electrical signals and the position indicating signals from the scanning means to produce on an output screen 22 a visual representation of internal structure of the subject. The system functions in accordance with a known form of ultrasonic scanning known as pulsed real time "B-scanning".

The transducer scanning means and position indicating apparatus and circuitry, the imaging electronics 16 and the display apparatus 18 suitably comprise circuitry and structure disclosed in the above incorporated patent application and article.

In addition to B-scanning capability, the system 10 can optionally also provide for a known form of so-called "Doppler" operation, which is useful in determining blood flow characteristics of examined arterial structure of a patient.

Figure 3:
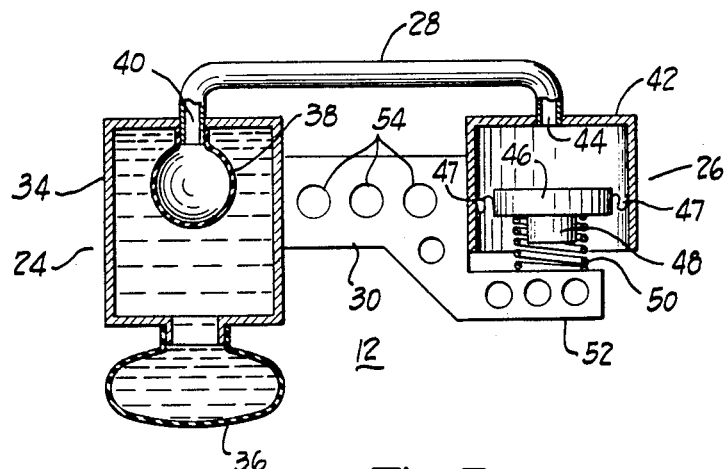
FIG. 3 is an elevational view, partially in cross section, showing a specific embodiment of a portion of the system illustrated in FIG. 2.

FIG. 3 illustrates specific construction of an ultrasonic probe assembly 12 made in accordance with this invention. The probe assembly 12 includes a transducer coupling section 24, a passive pressure compensation section 26, fluid conduit structure 28 communicating between the sections 24, 26, and suitable connecting structure 30 for holding the sections 24, 26 rigid with respect to one another, and for affording a convenient manual grip on the transducer probe assembly.

The coupling section 24 suitably comprises a cylinder 34 for defining a chamber for containing a fluid coupling medium, such as water. The chamber described by the cylinder 34 communicates with a highly resilient coupling bag 36, also filled with the fluid medium, which serves as the subject contacting element of the probe assembly for affording an efficient fluid coupling to enable ultrasonic energy propagated by the transducer within the fluid medium to efficiently enter the patient's body. The chamber described by the structure 34 has located within it the ultrasonic transducer element. The piezoelectric transducer element is located in accordance with known technology but, for simplicity and easy interpretation of the inventive features shown in these drawings, it is not shown here.

The cylinder 34 also includes a resilient gas reservoir 38, which communicates with an aperture 40 in the end of the cylinder 34 opposite the coupling bag 36. The interior of the compliant air reservoir 38 communicates with the conduit 28, which is a suitable piece of substantially rigid tubular material, such as metal, fiberglass or the like. The end of the conduit 28 opposite the reservoir 38 communicates with a chamber defined by a generally cylindrical structure 42 which comprises a portion of the compensating section 26. The communication between the conduit 28 and the chamber defined by the structure 42 is by way of an aperture 44.

Within the chamber described by the cylinder 42, a piston 46 is slidably disposed. A known "rolling diaphragm" structure adapts the piston for very low friction sliding in the cylinder. The rolling diaphragm includes a flexible airtight membrane 47, annular in construction, attached between the periphery of the piston and the interior wall of the cylinder. The flexibility of the membrane 47 allows the piston to ride up and down within the cylinder without appreciable friction between the piston and the cylinder walls, since the piston can be made somewhat smaller in diameter than the inside cylinder diameter. Suitable structure is easily provided by one of ordinary skill to maintain the piston generally aligned in the cylinder. Such structure can comprise a weight 48 concentrically aligned within a coil spring 50 (discussed below). Supplemental structure, such as a downwardly extending axial rod attached to the piston and a cooperating fixed axial sleeve to receive the rod, can also be provided.

The piston also includes a weight 48 attached to its lower side. The mass of the weight 48 is selected such that its mass, along with the mass of the piston 46, precisely counterbalances the weight of the water coupling medium within the cylinder 34 when the probe assembly 12 is held in an upright position, such as illustrated in FIG. 3.

A compression coil spring 50 extends from an arm 52 of the rigid connecting structure 30, and presses upwardly against the piston 46, as illustrated in FIG. 3. The spring rate of the spring 50, and its length and location, are selected such that the pressure increment applied by the biasing of the piston 46 represents the amount of pressure which is considered desirable for exertion by the coupling bag 36 upon the skin of a patient to be examined.

It has been determined that a suitable coupling pressure can be as low as approximately 0.07 pounds per square inch gauge. Such a low pressure minimizes risks that examination of a patient by impingement upon his blood vessels within the coupling bag 36 will cause complications.

Another important aspect of the probe of FIG. 3 is that the very low coupling pressure exerted by the coupling bag 36 on the patient is maintained substantially constant, irrespective of changes in the orientation of the probe assembly 12. When, for example, the probe assembly 12 is in the position indicated in FIG. 3, the weight of the head of water within the chamber 34 and the bag 36 is just counterbalanced by the negative (gauge) air pressure exerted by the weighted piston 46 (offset by the small force applied by the spring 50). If, for example, the probe assembly 12 were to be inverted such that the bag 36 extended upwardly, the weighted piston would exert a positive air pressure on the compliant air reservoir 38 and maintain the bag 36 at the same pressure as when the bag was disposed as in FIG. 3. For intermediate orientations between these two extremes, the weighted piston and the weight of the coupling medium cooperate to maintain the pressure on the bag 36 at a substantially constant level. The pressure stabilization is achieved by apparatus completely self-contained in the probe assembly and does not require any external or active pressure regulating components.

An advantage of using air, rather than water, in the pressure compensating portion of the probe, is that the probe weight required is less than if the entire coupling and compensation sections contained water. In addition, the use of air allows the compensating action to occur very rapidly upon a change of position since the gaseous medium has much lower viscosity as compared to a liquid medium.

Figure 4:
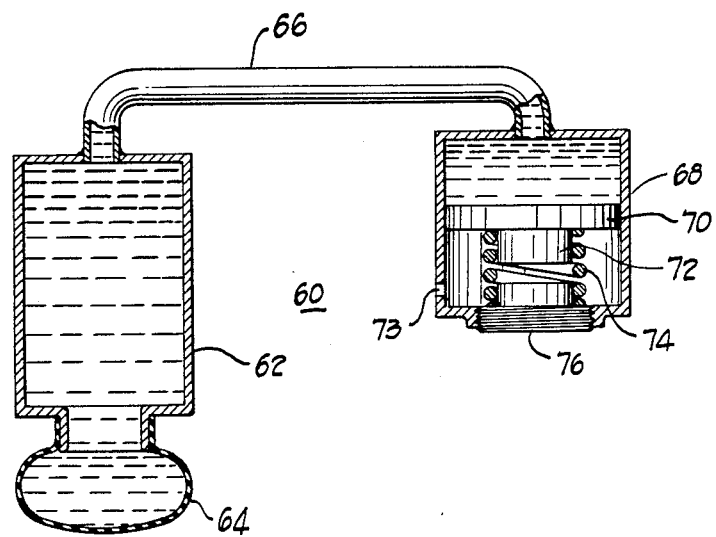
FIG. 4 is an elevational view, partly in cross section, illustrating another specific embodiment of a portion of the system of FIG. 2.

FIG. 4 shows another simpler embodiment of an ultrasonic probe assembly 60. The coupling section comprises a cylinder 62 which communicates on one end with a coupling bag 64 and on the other with a conduit 66. The compensation section includes a cylinder 68 with a slidably disposed piston 70 and a weight 72 attached thereto and of predetermined mass. In this embodiment, the coupling bag 64, cylinder 62, conduit 66 and cylinder 68 each contain a fluid coupling medium such as water. The combined weight of the piston 70 and the weight 72 is selected such that, when the probe assembly of FIG. 4 is in its upright attitude, the piston 70 and weight 72 completely counterbalance the weight of the water in the remainder of the system, such that the gauge pressure on the coupling bag is zero. An air vent 73 is provided beneath the piston to allow free piston movement. The piston is coupled to the cylinder walls by the above described "rolling diaphragm" structure. A compression coil spring 74 is situated between the bottom of the piston 70 and the floor of the cylinder 68, to exert a small force upwardly on the piston-weight combination. The force exerted by the spring 74 can be altered as desired by rotating a threaded plug 76 which is located in a threaded hole in the bottom of the cylinder 68. As the plug 76 is rotated to advance it further into the cylinder, the upward force exerted on the piston by the spring 74 increases, such that the pressure exerted on the coupling bag 64 also increases to some predetermined level. The pressure exerted by the coupling bag 64, because of the weighted pistons 70, 72, remains substantially constant, irrespective of the spatial orientation of the probe assembly 60.

Figure 5:
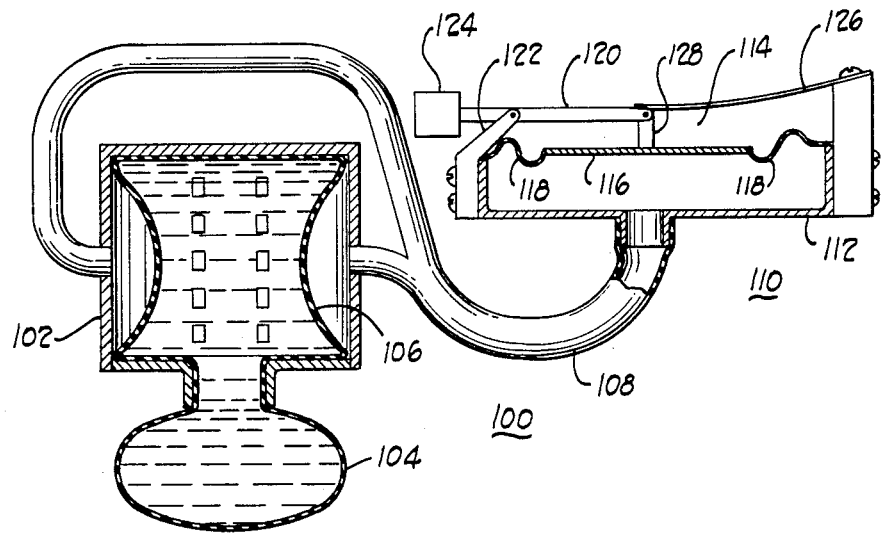
FIG. 5 is an elevational view, partially in cross section, illustrating still another embodiment of the portion of the system of FIG. 2.

FIG. 5 shows still another embodiment of a passive pressure compensated ultrasonic probe. In FIG. 5, a probe assembly 100 is illustrated. The coupling section includes a cylinder 102 which communicates as its lower end with a coupling bag 104. Within the cylinder 102, and in gas tight communication with the bag 104, is a cheek pouch reservoir 106 made of resilient gas impervious material. The cheek pouch reservoir effectively lines the interior of the cylinder 102 and becomes the wall of the bag 104.

A gas conduit system 108 communicates with the interior of the cylinder 102, but exteriorly with respect to the cheek pouch reservoir 106. When gas pressure is applied to the conduit system 108, it causes the cheek pouch reservoir to partially collapse inwardly within the cylinder 102, applying increased pressure to the fluid medium within the pouch reservoir 106 and the bag 104.

The conduit system 108 has its input connected to the output of a pressure compensation section 110. The pressure compensation section 110 includes structure 112 defining a cylinder and a diaphragm pump 114 for exerting pressure on gas within the cylinder 112. The diaphragm pump 114 consists of a loose fitting piston 116 with its periphery coupled to the walls of the cylinder 112 by means of a flexible gas impervious diaphragm 118 extending therearound.

Pressure on the piston 116 is governed by a mechanical lever structure, including a lever 120 pivoted about the end of an arm 122 at one end attached to a rod 128, and having a weight 124 connected to its end. The dimensions of the lever system and the mass of the weight 124 are chosen in order that the pressure exerted by the diaphragm pump on the interior of the cylinder 102 by way of the conduit 108 is just sufficient to maintain a gauge pressure of zero within the bag 104. In this instance, as illustrated in FIG. 5, the weight 124 causes the lever 120 to pull upwardly on the piston 116, such that the gauge pressure within the cylinder 112 and the conduit 108 is negative, tending to pull the cheek pouch reservoir 106 outwardly toward the walls of the cylinder 102.

A leaf spring 126 mounted on a housing surrounding the cylinder 112 is disposed to resiliently press downwardly upon the rod 128 attached to the piston member 116 of the diaphragm pump. The resiliency and placement of the leaf spring 126 is chosen such that the pressure exerted by the diaphragm pump in response to the force exerted by the leaf spring equals the desired pressure at the coupling bag 104.

In a manner similar to the operation of the above described embodiments, the embodiment of FIG. 5 provides a passive, gravity responsive structure for maintaining the pressure in the bag 104 at a uniformly low level, irrespective of the spatial orientation of the probe assembly 100.

It is to be understood that the descriptions of the above specific embodiments are intended to be illustrative rather than exhaustive of this invention. Persons of ordinary skill may make changes, additions to, or deletions from the embodiments shown, without departing from the spirit of this invention, or its scope, as defined in the appended claims.

What is claimed is:

1. A mobile fluid coupled ultrasonic probe assembly comprising:
   (a) an ultrasonic transducer;
   (b) apparatus including a reservoir containing a fluid medium in communication with the transducer and including a subject contact portion for fluid coupling the transducer to a subject, the contact portion being coupled to the fluid medium and adapted for exerting a pressure on the subject which is a function of both the pressure on the fluid medium and the rotational orientation of the mobile probe assembly, and
   (c) passive pressure compensating apparatus coupled to the fluid medium and having means for varying the pressure on the fluid medium as a function of rotational orientation of the mobile probe assembly.

2. The assembly of claim 1, wherein the passive pressure compensating apparatus comprises:
   (a) a cylinder fixed relative to the reservoir;
   (b) a piston slidably mounted in the cylinder and fluidically coupled to the fluid medium, and
   (c) resilient means for biasing the piston toward compression of the fluid medium.

3. The assembly of claim 1, wherein:
said subject contact portion comprises a compliant membrane.

4. A mobile fluid coupled ultrasonic probe assembly comprising:
   (a) an ultrasonic transducer;
   (b) structure defining a first chamber communicating with the transducer and having a compliant subject contact membrane and containing a fluid medium for fluid coupling the transducer to the membrane;
   (c) structure defining a second substantially cylindrical chamber rigidly oriented with respect to said first chamber;
   (d) conduit means communicating between the first and second chambers;
   (e) a piston slidably disposed within said second chamber, and
   (f) resilient biasing means coupled to the piston for biasing said piston in a direction substantially axial to said cylindrical chamber tending to compress the fluid medium.

5. The assembly of claim 4, wherein said resilient biasing means includes structure having means for adjusting its resiliency coefficient.

6. The assembly of claim 4, wherein said fluid medium is disposed to substantially fill said first and second chambers and said conduit means.

7. The assembly of claim 4, wherein said fluid coupling medium comprises a liquid.

8. The assembly of claim 4, wherein said fluid coupling medium comprises water.

9. The assembly of claim 4, further comprising:
a weight attached to said piston.

10. A mobile ultrasonic probe assembly comprising:
   (a) an ultrasonic transducer;
   (b) structure defining a first chamber communicating with the transducer and having a compliant coupling bag also communicating with the first chamber and adapted for effecting subject contact and for fluid coupling said transducer to said coupling bag;
   (c) a fluid medium disposed in said coupling bag and said first chamber;
   (d) structure defining a second substantially cylindrical chamber;
   (e) a gas filled structure communicating with the second chamber for effecting pressure coupling between said first and second chambers, and including a compliant reservoir contacting the fluid medium;

(f) a piston slidably disposed in said second chamber, and (g) resilient structure including means for biasing said piston toward compression of said gas.

11. The assembly of claim 10, further comprising: a weight of predetermined mass attached to said piston.

12. The assembly of claim 10, wherein said fluid coupling medium comprises water, and said gas comprises air.

13. The assembly of claim 10, wherein said resilient biasing structure includes apparatus having means adapted for adjusting its resiliency coefficient.

14. A mobile ultrasonic probe assembly comprising:
(a) an ultrasonic transducer;
(b) structure defining a first chamber communicating with the transducer;
(c) a compliant subject coupling bag also communicating with the first chamber;
(d) a fluid medium within the first chamber and coupling bag for acoustically coupling the transducer and the bag;
(e) a cheek pouch reservoir contacting the fluid medium within the first chamber;
(f) a gas filled conduit leading from external of the first chamber to the cheek pouch reservoir;
(g) a diaphragm pump coupled to the conduit for exerting pressure on the gas in said conduit and said cheek pouch reservoir;
(h) a gravity responsive mechanical weight and linkage structure coupled to the diaphragm pump for varying the pressure on the gas applied by said diaphragm pump as a function of the orientation of said probe assembly.

15. An ultrasonic system comprising:
(a) an ultrasonic transducer;
(b) apparatus including a reservoir communicating with the transducer and containing a fluid medium and including a subject contact portion for fluid coupling the transducer to a subject, the contact portion being coupled with the fluid medium and adapted for exerting a pressure on the subject which is a function of the pressure on the fluid medium;
(c) slidable gravity responsive passive pressure compensating means for varying the pressure on the fluid medium as a function of rotational orientation of the fluid medium containing apparatus;
(d) power circuitry coupled to the transducer for actuating the transducer to propagate incident ultrasonic energy into the subject;
(e) transducer axis scanning and position indicating circuitry including variable electric signal producing means and other apparatus mechanically coupled between the electric signal producing means and the transducer, and imaging electronics, coupled to the scanning circuitry and apparatus for processing electrical signals produced by the transducer, and the variable electrical signals produced by the scanning and position indicating circuitry and apparatus, and
(f) display apparatus including a cathode ray tube imaging device responsive to the processed electrical signals and the position indicating circuitry for producing an ultrasonically derived visual image of internal structure of the subject.

16. A mobile fluid coupled ultrasonic probe assembly comprising:
(a) an ultrasonic transducer;
(b) apparatus defining a reservoir containing a fluid medium communicating with the transducer and including a subject contact portion communicating with the reservoir for fluid coupling the transducer to a subject, the contact portion comprising structure including means for exerting a force on the subject which is a function of the pressure on the fluid medium, and
(c) gravity actuated passive pressure compensation apparatus fixed relative to said transducer and including means for varying pressure on the fluid medium as a function of rotational orientation of the assembly.

17. An ultrasonic investigation method comprising the steps of:
(a) directing ultrasonic energy into a subject for examination by use of a fluid medium coupled to a subject contact element, said contact element having means for exerting a force on the subject which is a function of the pressure on the fluid medium;
(b) varying the pressure on the fluid medium in response to gravity as a function of the rotational orientation of the subject contact element, and
(c) producing a visual representation of internal subject structure in response to echoes from the ultrasonic energy introduced into the subject.

18. A mobile fluid coupled ultrasonic probe assembly comprising:
(a) an ultrasonic transducer;
(b) apparatus defining a reservoir communicating with the transducer and containing a fluid medium and including a subject contact portion also communicating with the reservoir and adapted for fluid coupling the transducer to a subject, the contact portion having structure including a resilient membrane for exerting a force on the subject which varies as a function of probe assembly orientation and of the pressure on the fluid medium. and
(c) slidable gravity responsive passive pressure compensating means for varying the pressure on the fluid medium as a function of rotational orientation of the probe assembly, said pressure variation maintaining the pressure exerted on the subject by the contact portion at a substantially uniform level, and substantially less than 0.5 pounds per square inch gage, substantially independent of probe assembly rotational orientation.

19. The assembly of claim 18, wherein said passive pressure compensating means includes means for maintaining the pressure exerted on the subject by the contact portion at approximately 0.07 pounds per square inch gage, irrespective of the orientation of the assembly.

* * * * *